(12) United States Patent
Ewen

(10) Patent No.: US 6,369,175 B1
(45) Date of Patent: *Apr. 9, 2002

(54) PROCESS FOR PRODUCING HEMIISOTACTIC POLYPROPYLENE

(75) Inventor: John A. Ewen, Houston, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/663,469

(22) Filed: Jun. 17, 1996

Related U.S. Application Data

(60) Continuation of application No. 07/695,139, filed on May 3, 1991, now abandoned, which is a division of application No. 07/419,221, filed on Oct. 10, 1989, now Pat. No. 5,036,034.

(51) Int. Cl.$^7$ .......................... C08F 4/44; C08F 110/06
(52) U.S. Cl. ...................... 526/114; 526/119; 526/160; 526/351; 526/943
(58) Field of Search ................................. 526/160, 114, 526/119, 351, 943

(56) References Cited

U.S. PATENT DOCUMENTS

| | | | | |
|---|---|---|---|---|
| 4,892,851 A | * | 1/1990 | Ewen et al. | 526/160 |
| 4,931,417 A | * | 6/1990 | Miya et al. | 526/127 |
| 4,937,299 A | * | 6/1990 | Ewen et al. | 526/114 |
| 5,416,178 A | * | 5/1995 | Winter et al. | 526/127 |
| 6,197,902 B1 | * | 3/2001 | Dolle et al. | 526/160 |
| 6,225,425 B1 | * | 5/2001 | Dolle et al. | 526/127 |

FOREIGN PATENT DOCUMENTS

| | | | |
|---|---|---|---|
| EP | 277004 | * | 8/1988 |

* cited by examiner

Primary Examiner—David W. Wu
Assistant Examiner—R. Rabago
(74) Attorney, Agent, or Firm—William D. Jackson

(57) ABSTRACT

This invention is for a metallocene compound which can be used in a catalyst system to produce hemiisotactic polymer. The compound is a bridged metallocene compound having dissimilar cyclopentadienyl groups and no bi-lateral symmetry. One example of the compound is isopropylidene(3-methylcyclopentadienyl-1-fluorenyl) zirconium dichloride. The catalyst of this invention can be converted to an ionic metallocene catalyst by an ionizing agent, such as methylaluminoxane. The polymer produced with this catalyst is characterized by having an isotactic structure effecting only every other asymmetric carbon atom. In the case of polypropylene, every other methyl group is on the same side of the principal polymer chain as represented by a Fisher projection. The remaining methyl groups can be either on the same side or on the opposite side of the principal polymer chain. The polymer produced with the catalyst of this invention can be used as a plasticizer.

2 Claims, No Drawings

PROCESS FOR PRODUCING HEMIISOTACTIC POLYPROPYLENE

This is a Continuation application of copending application Ser. No. 07/695,139, filed on May 3, 1991, now abandoned, which is a Division of application Ser. No. 07/419,221, filed on Oct. 10, 1989, now issued as U.S. Pat. No. 5,036,034.

BACKGROUND OF THE INVENTION

1. Field of the Invention

This invention relates, generally, to a catalyst system. Specifically, this invention relates to hemiisospecific catalysts.

2. Description of Related Art

Olefins, especially propylene, may be polymerized to form polyolefins in various forms: isotactic, syndiotactic and atactic. Isotactic polypropylene contains principally repeating units with identical configurations and only a few erratic, brief inversions in the chain. Isotactic polypropylene may be structurally represented in a Fischer projection as (1)

In Bovey's NMR nomenclature the isotactic structure is designated . . . mmmm . . . since the five successive methyl groups are meso to each other, i.e., on the same side of the plane in a Fischer projection.

Isotactic polypropylene is capable of being a highly crystalline polymer with a high melting point and other desirable physical properties that are considerably different from the polymer in an amorphous (noncrystalline) state.

A syndiotactic polymer contains principally units of exactly alternating stereoisomers and is represented in a Fischer projection by the structure:

(2)

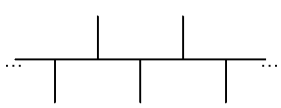

In Bovey's NMR nomenclature the syndiotactic structure is designated . . . rrrr . . . since the five successive methyl groups are racemic to each other, i.e., on alternate sides of the plane in a Fischer projection.

A polymer chain showing no regular order of repeating unit configurations is an atactic polymer. In commercial applications, a certain percentage of atactic polymer is typically produced with the isotactic form.

There are other variations in the form of polymer structure. Hemiisotactic or hemitactic polypropylene was disclosed in "Hemitactic Polypropylene: An Example of a Novel Kind of Polymer Tacticity" by M. Farina, G. Di Silvestro and P. Sozzani (Macromolecules, Vol. 15, 1451–1452, 1982). The structure of hemiisotactic polymers is represented in a Fischer projection as follows:

(3)

The monomeric unit of the polymer is of the following structure:

(4)

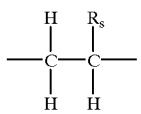

where $R_S$ is a hydrocarbyl group or nonhydrocarbyl group. The second carbon atom in formula (6) is the asymmetric carbon atom, i.e., the one which does not have identical groups attached, hence "asymmetric".

The structure of the polymer is characterized by $R_S$ groups attached to every other asymmetric carbon atom being on the same side of the principal polymer chain as represented in a Fischer projection and $R_S$ groups attached to the remaining asymmetric carbon atoms being either on the same side or the opposite side of the $R_S$ groups attached to every other asymmetric carbon atom. When $R_S$ groups are on the same side of the principal polymer chain, the structure is isotactic. Since only every other one conforms to the isotactic structure, it is "hemi". The material is a noncrystalline polymer.

Polymerization of olefins is primarily with Zeigler-Natta catalysts one family of Zeigler-Natta catalysts is Group IV metallocene compounds with methylaluminoxane as a cocatalyst. German patent application No. 2,608,863 discloses a catalyst system for the polymerization of ethylene consisting of bis(cyclopentadienyl)titanium dialkyl, an aluminum trialkyl and water. German patent application No. 2,608,933 discloses an ethylene polymerization catalyst system consisting of zirconium metallocenes of the general formula $(cyclopentadienyl)_n ZrY_{4-n}$, wherein Y represents $R_1 CH_2 AlR_2$, $CH_2 CH_2 AlR_2$ and $CH_2 CH(AlR_2)_2$ where R stands for an alkyl or metallo alkyl, and n is a number within the range 1–4; and the metallocene catalyst is used in combination with an aluminum trialkyl cocatalyst and water.

The use of metallocenes as catalysts in the copolymerization of ethylene and other alpha-olefins is also known in the art. U.S. Pat. No. 4,542,199 to Kaminsky, et al. discloses a process for the polymerization of olefins and particularly for the preparation of polyethylene and copolymers of polyethylene and other alpha-olefins. The disclosed catalyst system includes a catalyst of the formula $(cyclopentadienyl)_2 MeRHal$ in which R is a halogen, a cyclopentadienyl or a $C_1$–$C_6$ alkyl radical, Me is a transition metal, in particular zirconium, and Hal is a halogen, in particular chlorine. The catalyst system also includes an alumoxane having the general formula $Al_2 OR_4 (Al(R)—O)n$ for a linear molecule and/or $(Al(R)—O)_{n+2}$ for a cyclic molecule in which n is a number from 4–20 and R is a methyl or ethyl radical. A similar catalyst system is disclosed in U.S. Pat. No. 4,404,344.

U.S. Pat. No. 4,530,914 discloses a catalyst system for the polymerization of ethylene to polyethylene having a broad molecular weight distribution and especially a bimodal or multimodal molecular weight distribution. The catalyst system is comprised of at least two different metallocenes and an alumoxane. The patent discloses metallocenes that may have a bridge between two cyclopentadienyl rings with the bridge serving to make those rings stereorigid.

European Patent Publication No. 0185918 discloses a stereorigid, chiral zirconium metallocene catalyst for the polymerization of olefins. The application does not indicate that hafnium could be substituted for the zirconium and used to produce a useful polymer product. The bridge between the cyclopentadienyl groups is disclosed as being a linear hydrocarbon with 1–4 carbon atoms or a cyclical hydrocarbon with 3–6 carbon atoms.

European Patent Application 0-277-003 relates to work by Turner on a catalyst prepared by a protonation method. A bis(cyclopentadienyl) metal compound is combined with a compound having a cation capable of donating a proton and an anion having a plurality of boron atoms. For example, the following reaction illustrates the invention:

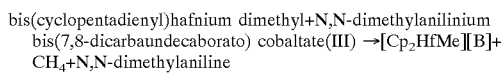

bis(cyclopentadienyl)hafnium dimethyl+N,N-dimethylanilinium bis(7,8-dicarbaundecaborato) cobaltate(III) →[Cp$_2$HfMe][B]+ CH$_4$+N,N-dimethylaniline where [B] is 7,8-dicarbaundecaborane.

European Patent Application 0-277-004 also relates to work by Turner on a catalyst prepared by a protonation method. A bis(cyclopentadienyl) metal compound is combined with an ionic compound having a cation which will irreversibly react with a ligand on the metal compound and an anion having a plurality of lipophilic radicals around a metal or metalloid ion. For example, the following reaction illustrates the invention:

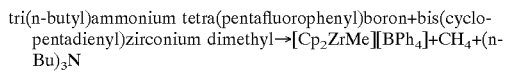

tri(n-butyl)ammonium tetra(pentafluorophenyl)boron+bis(cyclopentadienyl)zirconium dimethyl→[Cp$_2$ZrMe][BPh$_4$]+CH$_4$+(n-Bu)$_3$N A system for the production of isotactic polypropylene using a titanium or zirconium metallocene catalyst and an alumoxane cocatalyst is described in "Mechanisms of Stereochemical Control in Propylene Polymerization with Soluble Group 4B Metallocene/Methylalumoxane Catalysts," J. Am. Chem. Soc., Vol. 106, pp. 6355–64, 1984. The article shows that chiral catalysts derived from the racemic enantiomers of ethylene-bridged indenyl derivatives form isotactic polypropylene by the conventional structure predicted by an enantiomorphic-site stereochemical control model. The meso achiral form of the ethylene-bridged titanium indenyl diastereomers and achiral zirconocene derivatives, however, produce polypropylene with a purely atactic structure.

SUMMARY OF THE INVENTION

In accordance with the present invention, there is provided a metallocene compound having a general formula of $$R''(C_pR_n)(C_pR'_m)MHal_2 \tag{5}$$

where each R and R' is a hydrocarbyl radical having from 1–20 carbon atoms, is the same or different and is selected such that CpR'm is a sterically different ring from CpRn resulting in a lack of bi-lateral symmetry for the compound, R'' is a structural bridge imparting stereorigidity to the compound, M is a Group 4 metal, n is from 0 to 4, m is from 0 to 4 and Hal is a halogen. One example of such a compound is isopropylidene (3-methylcyclopentadienyl-1-fluorenyl)zirconium dichloride. This compound is a bridged, metallocene compound having dissimilar cyclopentadienyl groups and no bi-lateral symmetry.

One use for these compounds is in a metallocene catalyst system. The metallocene compounds defined above can be activated as catalysts by any known method of metallocene catalyst preparation The polymer produced with the catalyst of this invention has the structure termed "hemiisotactic". Hemiisotactic polypropylene is characterized by every other methyl group being on the same side of the principal polymer chain as represented by a Fischer projection. The remaining methyl groups can be either on the same side or the opposite side of the principal polymer chain.

Propagation of the polymer chain results from head-to-tail linkage of the propylene monomer units in such a way the following structure is formed:

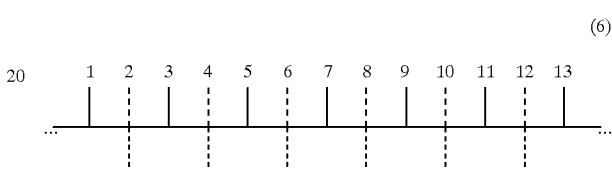

(6)

In this Fischer projection representation the odd numbered methine units are meso with respect to each other and the even numbered methine carbons have random steric configurations. Hemiisotactic polypropylene is noncrystalline due to the disorder and irregularity of these random groups.

DESCRIPTION OF THE INVENTION

The invention is for a new metallocene compound which is a catalyst precursor for a catalyst used to produce polymers termed hemiisotactic. The metallocene compound is changed to a metallocene catalyst with an ionizing agent which converts the neutral metallocene compound to a metallocene cation which operates as a catalyst. The ionizing agent can be a cocatalyst compound such as methylaluminoxane (MAO).

A preferred application of the invention is in the hemiisotactic polymerization of monomers which may be characterized in terms of the following formula:

$$CH_2=CH-R_S \tag{7}$$

wherein $R_S$ is a hydrocarbyl group or nonhydrocarbyl substituent. Monomers to which the present invention is applicable are $C_3$+ alpha olefins, 1-butene, 1-dienes, such as 1,3-butadiene, substituted vinyl compounds, such as vinyl chloride, and styrene. The preferred application is to ethenically unsaturated monomers. By the term "ethenically unsaturated monomer" as used herein is meant a hydrocarbon or substituted hydrocarbon compound characterized by a terminal vinyl group ($CH_2=CH-$). The most preferred ethenically unsaturated compounds employed in the present invention have at least three carbon atoms. A specific example is propylene.

The catalyst used to produce hemiisotactic olefins is from a metallocene compound having a general formula of $$R'' (CpR_n)(CpR'_m)MHal_2 \tag{8}$$

where Cp is cyclopentadienyl or substituted cyclopentadienyl, each R and R' is a hydrocarbyl radical having from 1–20 carbon atoms and is the same or different and is selected such that $CpR'_m$ is a sterically different ring from $CpR_n$ resulting in a lack of bi-lateral symmetry for the compound, R" is a structural bridge imparting stereorigidity to the compound, M is a Group 4 metal, preferably titianium, zirconium or hafnium, n is from 0 to 4, m is from 0 to 4 and Hal is a halogen, preferably chlorine.

The lack of bi-lateral symmetry for the compound is defined as the condition in which a metallocene compound having one non-cyclopentadienyl coordination site has no substituents or one or more substituents on one side of the cyclopentadienyl rings both above and below the coordination site and one or more substituents on the other side of the cyclopentadienyl rings either above or below the coordination site. One example of such a compound is isopropylidene (3-methylcyclopentadienyl -1-fluorenyl)zirconium dichloride, abbreviated iPr(3MeCp-1-Flu)ZrCl$_2$. An illustration of the ligand of this compound is shown below:

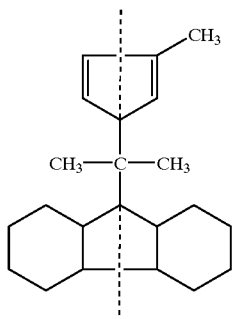

(9)

The lack of bi-lateral symmetry is illustrated by the right side of the drawing being different from the left because one methyl group is on the right side of one cyclopentadienyl ring and no substituents are on the left side of the same cyclopentadienyl ring.

The iPr(3MeCp-1-Flu)ZrCl$_2$ compound was prepared by cracking the methylcyclopentadiene diner, preparing 3,6,6-trimethylfulvene, bridging the two cyclopentadiene compounds with an isopropylidene bridge and forming a coordination compound with zirconium and chlorine. Final reactions were carried out in tetrahydrofuran (THF) and in methylenedichloride (MeCl$_2$), also known as dichloromethane. Use of MeCl$_2$ allows the iPr(3MeCp-1-Flu) ZrCl$_2$ to be isolated in pure form.

Polymerization of the olefin is accomplished by any of the known means for polymerization of olefins with metallocene catalysts, for example polymerization in bulk, slurry or gas phase. For polypropylene, polymerization temperatures range from −80° C. to 150° C., preferably 25° C. to 90° C. and most preferably from 50° C. to 80° C.

The noncrystalline hemiisotactic polypropylene has use as a plasticizer for syndiotactic or isotactic polypropylene. A plasticizer is a material incorporated in a plastic to increase its workability and its flexibility or distensibility. The addition of a plasticizer may lower the melt viscosity, the temperature of the second-order transition, or the elastic modulus of the plastic. The plastic and plasticizer are intimately mixed which is most commonly done by heating until the plastic has dissolved into the plasticizer of vice versa. Alternatively, the plastic and plasticizer are mixed by dissolution in a common solvent without heat followed by removal of the solvent by evaporation.

Hemiisotactic polymer is noncrystalline and with its partial stereoregular structure would have properties of a plasticizer. A specific example of a -hemiisotactic polymer as a plasticizer is a reactor blend of hemiisotactic polypropylene and syndiotactic polypropylene made by polymerizing propylene simultaneously with both iPr(3MeCp-1-Flu)ZrCl$_2$ and isopropylidene (cyclopentadienyl -1-fluorenyl) zirconium dichloride, abbreviated iPr(Cp-1-Flu)ZrCl$_2$, or any other syndiospecific catalyst precursor. A reactor blend of hemiisotactic and isotactic polypropylene is possible by polymerizing propylene simultaneously. with both iPr (3MeCp-1-Flu)ZrCl$_2$ and ethylenebis(tetrahydroindenyl) zirconium dichloride, abbreviated Et(IndH$_4$)$_2$ZrCl$_2$, or any other isospecific catalyst precursor. The amount of hemiisotactic polypropylene in mixture with isotactic or syndiotactic polypropylene can range from 1–90% by weight, depending on desired physical properties of the plasticized plastic. Preferably, the amount of hemiisotactic polypropylene in mixture with isotactic or syndiotactic polypropylene ranges from 5–50% by weight. Most preferably, the amount of hemiisotactic polypropylene in mixture with isotactic or syndiotactic polypropylene is approximately 10% by weight.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE I

A. Preparation of 3,6,6,-trimethylfulvene 150 ml of methylcyclopentadiene dimer was fractionally distilled from 100 ml of mineral oil and at 62° C. and collected at 0° C. 500 mmol of methyl lithium (1.4M; diethylether) were added, dropwise, to a mixture of 500 mmol of freshly distilled methylcyclopentadiene and 137 ml of dry acetone at 0° C. The solution was stirred for 1 hour at 25° C. 8 g (85% yield) of 3,6,6-trimethylfulvene were recovered from the organic layer by vacuum distillation after an extraction with 100 ml of saturated, aqueous NH$_4$Cl and drying over MgSO$_4$.

B. Preparation of iPr(3-MeCp-1-Flu)

One mole of 3,6,6-trimethylfulvene was dissolved in 100 ml THF and added, dropwise, to cold (−78° C.) solution containing 1 mol of the lithium salt of the fluorenyl anion in approximately 100 ml THF and 714 ml of diethyl ether. The mixture was warmed to room temperature. 18 g of white powder were obtained from the organic layer as a single isomer by extracting with aqueous NH$_4$Cl, drying over MgSO$_4$, filtering concentrating under vacuum to an oil, dissolving in chloroform, precipitating and washing with excess methanol. $^1$H NMR CD$_2$Cl$_2$, int. ref. Me$_4$Si delta=0 ppm: 7.7d, 7.3t, 7.2d and 7.1t (8) (Flu C6 rings); 6.5t and 5.6d (2) (Cp vinyl); 4.1s (1) (Flu C5 ring methine); 2.95s (2) (Cp methylene); 2.2d (3) (Cp methyl); 1.0s (6) (isopropyl methyl). (1 stereoisomer: The Cp metheylene signal appears as a singlet because the methylene group is alpha to both the iPr bridge and the Cp methyl).

C1. Preparation of isopropylidene(3-methylcyclopentadienyl -1-fluorenyl)zirconium dichloride in methylene chloride 2 equivalents of methyllithium (1.4 M in diethylether) were added, dropwise, at −78° C. to 5 g of isopropylidene (3-methylcyclopentadiene-1-fluorene) dissolved in 100 ml THF, warmed to 25° C., and stirred for 12 hours. The red dilithio salt was isolated by evaporating the solvents under vacuum and then purified by washing with two 150 ml portions of dry, deoxygenated pentane that were cannulated away in term. The dianion was dissolved in methylene chloride at −78° C. and an equivalent of $ZrCl_4$, slurried in 125 ml $CH_2Cl_2$ at −78° C., was rapidly cannulated into the flask containing the soluble dianion. The stirred mixture was warmed slowly to 25° C. and stirred for 12 hours. A white solid was filtered off. 3 g of a moderately air sensitive, orange powder were obtained by concentrating the methylene chloride under vacuum, cooling the −20° C. for 12 hours and cannulating the supernatant away. The product was purified by recystallizing it from methylene chloride. $ZrCl_2C_{22}H_{20}$ requires C, 59; H, 4.5. Found: C, 56; H, 4.4. $^1H$ NMR (delta, ppm) $CD_2Cl_2$, int. ref. TMS delta=0 ppm: 8.15–8.10 2d (2), 7.87–7.78 2d (2), 7.55–7.48 2t (2), 7.27–7.21 m (2) (Flu C6 rings); 5.93 t (1), 5.63 t (1), 5.42 t (1) (Cp vinyl); 2.4 d (6) (isopropyl methyl); 2.0 s (3) (Cp methyl).

C2. Preparation of isopropylidene(3-methylcyclopentadiene -1-fluorenyl)zirconium dichloride in THF 34 mmol methyllithium in diethyl ether (1.4M) were added, dropwise, at 25° C., with stirring, to 5 gms of iPr[3-methylcyclopentadienyl-1-fluorene] ligand, then dissolved in 75 cc's THF which was contained in a round bottom flask equipped with a sidearm and dropping funnel. The dark orange/red solution was stirred for several hours after gas evolution had ceased. 6.41 gms of $ZrCl_4 \cdot 2$ THF were dissolved in 100 ml of THF at 40° C. The dianion was cannulated into the flask containing the $ZrCl_4 \cdot 2$ THF at 25° C. The mixture was stirred for 18 hours. The solution was then cannulated into a flask and cooled to −20° C. to obtain a crystalline product. Alternatively, the THF was evaporated under vacuum. 5 mg of the LiCl/iPr[3MeCp-1-Flu]$ZrCl_2$ mixture was added to MAO for a polymerization test.

EXAMPLE II 1.4 cc of methylaluminoxane (MAO) were mixed with 5 mg of iPr(3MeCp-1-Flu)$ZrCl_2$ prepared in THF as in Example I and dissolved in 10–20 ml of toluene. The MAO was 37 weight percent (Scherring). 1.2 liter of propylene was added to the reactor. The mixture was stirred for 10 minutes. Reactor temperature was set at 60° C.

The catalyst solution was added to a 50 ml stainless steel bomb. 200 ml of propylene was pumped through the bomb into the reactor. The contents of the reactor were agitated for 60 minutes.

The reaction product was dried in a vacuum. The polymer was weighed and analyzed for molecular weight distribution. The results are shown in Table I.

EXAMPLE III

The procedure of Example II was repeated using 1.4 cc of MAO, 1.2 l of propylene, 5 mg of iPr(3MeCp-1-Flu)$ZrCl_2$, a reaction temperature of 30° C. and a run time of 60 minutes. The results are shown in Table I.

EXAMPLE IV

The procedure of Example II was repeated. using 1.4 cc of MAO, 1.2 l of propylene, 5 mg of iPr(3MeCp-1-Flu)$ZrCl_2$ prepared in MeCl$_2$ as in Example I, a reactor temperature of 65° C. and a run time of 60 minutes. The results are shown in Table I.

A C-13 NMR spectra was obtained for the polymer from this run. The probability of the occurrence of a particular sequence of meso and racemic polymer structures for hemiisotactic polypropylene was calculated based on the method in "Hemitactic Polypropylene: An Example of a Novel Kind of Polymer Tacticity". The results for the calculated versus the observed values as a function of the relative intensity of the NMR spectra are shown in Table II.

EXAMPLE V 5.0 cc of MAO were mixed with 5 mg of iPr(3MeCp-1-Flu)$ZrCl_2$ prepared in MeCl$_2$ as in Example I above and dissolved in 10–20 ml of toluene. The MAO was 10 weight percent (Scherring). 1.4 l of propylene was added to the reactor. The mixture was stirred for 10 minutes. Reactor temperature was set to 60° C.

0.4 mg of isopropylidene(cyclopentadienyl -1-fluorenyl) zirconium dichloride, abbreviated iPr(Cp-1-Flu)$ZrCl_2$, was dissolved separately in 10–20 ml of toluene. The two catalyst solutions were mixed together and added to a 50 ml stainless steel bomb. 200 ml of propylene was pumped through the bomb into the reactor. The contents of the reactor were agitated for sixty minutes.

The reaction product was dried in a vacuum. The polymer was weighed and analyzed for melting point. The results are shown in Table I.

All general synthetic procedures were performed under an inert atmosphere using a Vacuum Atmospheres glovebox or Schlenk techniques. Toluene, pentane and tetrahydrofuran solvents were distilled under nitrogen from purple sodium/benzophone-ketyl. Dichloromethane was distilled from fresh calcium hydride under nitrogen.

The following results are from the experimental runs described above using the method of the present invention.

TABLE I

| Example | Metallocene Compound mg | MAO cc's | Propylene l | T, ° C. |
|---|---|---|---|---|
| | iPr(3MeCp-1-Flu) ZrCl$_2$ | | | |
| 2 | 5 | 1.4 | 1.2 | 60 |
| 3 | 5 | 1.4 | 1.2 | 30 |
| 4 | 5 | 1.4 | 1.2 | 65 |
| | iPr(3MeCP-1-Flu)ZrCl$_2$/ iPr(Cp-1-Flu)ZrCl$_2$ | | | |
| 5 | 5/0.4 | 5.0 | 1.4 | 60 |

| Example | t, min. | Yield g | M$_w$/M$_n$ |
|---|---|---|---|
| 2 | 60 | 184 | 1.9 |
| 3 | 60 | 32 | |
| 4 | 60 | 297 | 3.4 |
| 5 | 60 | 162 | |

TABLE II

| Sequence | Calculated | Observed |
|---|---|---|
| mmmm | 0.15 | 0.14 |
| mmmr | 0.11 | 0.12 |
| rmmr | 0.07 | 0.06 |
| mmrr | 0.25 | 0.21 |
| xmrx | 0.00 | 0.05 |
| mrmr | 0.00 | 0.00 |
| rrrr | 0.23 | 0.19 |
| rrrm | 0.14 | 0.14 |
| mrrm | 0.06 | 0.08 |

This invention has taken a known syndiospecific catalyst precursor with bi-lateral symmetry and added a methyl group on one of the cyclopentadienyl groups to eliminate the bi-lateral symmetry. The new catalyst produces a structure of polypropylene termed hemiisotactic due to every other methyl group of the polypropylene being above the plane in a Fischer projection. Hemiisotactic polypropylene is non-crystalline and can be used as a plasticizer with syndiotactic and isotactic polypropylene.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letter of Patent of the United States is:

1. A process for polymerizing propylene, said process comprising:

a) selecting a metallocene compound described by the formula:

$$R''(CpR_n)(CpR'_m)MeHal_2$$

wherein $R''(CpR_n)(CpR'_m)$ is an isopropylidene (3-methylcyclopentadienyl-1-fluorenyl) radical; Me is a Group IVb, Vb, or VIb metal; each Hal is a halogen;

b) activating the metallocene compound as a metallocene catalyst with methylaluminoxane;

c) polymerizing propylene with the metallocene catalyst;

d) forming hemiisotactic polypropylene;

e) selecting a second metallocene compound described by the formula:

$$R''(CpR_n)(CpR'_m)MeHal_2$$

wherein $R''(CpR_n)(CpR'_m)$ is an isopropylidene (cyclopentadienyl-1-fluorenyl) radical; Me is a Group IVb, Vb, or VIb metal; each Hal is a halogen; and f) forming a reactor blend of hemiisotactic polypropylene and syndiotactic polypropylene.

2. A process for polymerizing propylene, said process comprising:

a) selecting a metallocene compound described by the formula:

$$R''(CpR_n)(CpR'_m)MeHal_2$$

wherein $R''(CpR_n)(CpR'_m)$ is an isopropylidene (3-methylcyclopentadienyl-1-fluorenyl) radical; Me is a Group IVb, Vb, or VIb metal; each Hal is a halogen;

b) activating the metallocene compound as a metallocene catalyst with methylaluminoxane;

c) polymerizing propylene with the metallocene catalyst;

d) forming hemiisotactic polypropylene;

e) selecting a second metallocene compound described by the formula:

$$R''(CpR_n)(CpR'_m)MeHal_2$$

wherein $R''(CpR_n)(CpR'_m)$ is an ethylenebis (tetrahydroindenyl) radical; Me is a Group IVb, Vb, or VIb metal; each Hal is a halogen; and f) forming reactor blend of hemiisotactic polypropylene and isotactic polypropylene.

* * * * *